US00PP14113P29

(12) United States Plant Patent
Lemon

(10) Patent No.: US PP14,113 P2
(45) Date of Patent: Aug. 26, 2003

(54) GERANIUM PLANT NAMED 'GLOBAL SALMON ROSE'

(75) Inventor: David Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,059

(22) Filed: Sep. 17, 2002

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Webb Ziesenheim Logsdon Orkin & Hanson, P.C.

(57) ABSTRACT

A new and distinct free and very early flowering ivy geranium plant with deep salmon pink colored flowers above deep green foliage having very good heat tolerance.

1 Drawing Sheet

Botanical classification: *Pelargonium×peltatum* (ivy geranium).

Varietal denomination: 'Global Salmon Rose'.

BACKGROUND OF THE INVENTION

The present invention comprises a new and distinct cultivar of *Pelargonium×peltatum* known by the varietal name 'Global Salmon Rose'. The new variety was discovered in a selected breeding program in Lompoc, Calif. as Breeder No. 6DG2879-2. The new variety is a result of cross breeding of 'Nicole' (female) (U.S. Plant Pat. No. 7,358) and an unnamed, unpatented plant (breeder no. 2068, male). The new variety exhibits similar plant type to the female parent and similar flower color to the male parent and has better flower color than the parents' flower colors. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 12 weeks from a rooted cutting to flowering in a 10 inch pot. The response time was determined on plants grown in soilless media employing constant fertilizer 200–250 parts per million of nitrogen and potassium in full light. Three cuttings planted in a pot and pinched at four weeks produces a finished hanging basket.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants were about 12 weeks old when described. The color readings were taken on a plant under 65–85 foot candles of fluorescent cool white light. Color references are primarily to The R.H.S. Colour Chart of The Royal Horticultural Society of London.

PLANT

Form: Compact, cascading mound.
Height: 18 cm from media surface to top of foliage in a 6 inch pot.
Diameter: 45 cm.
Strength: Does not require artificial support.
Rooting time: Roots visible to outside of a dirt plug in 10–14 days.
Leaves:
- *Attachment.*—Alternate.
- *Stipules.*—Two per node.
- *Size.*—Length: 4.0–5.5 cm. Width: 5.5–6.5 cm. Zone: 3–5 mm from petiole attachment; zone is 0.7–1 cm wide.
- *Shape.*—Reniform; cordate base, pointed apex.
- *Margin.*—Entire with lobes.
- *Texture.*—Leathery.
- *Pubescent.*—Slight.
- *Color.*—Upper surface: 137A. Lower surface: 138B. Zone: 187A.
- *Ribs and veins.*—Venation: Palmate. Color: 144A.

Petioles:
- *Color.*—144A.
- *Length.*—3–5.5 cm.

Stem:
- *Color.*—144A.
- *Length.*—25 cm.
- *Internode length.*—2–4 cm.

THE BUD

Shape when no color showing:
- *Overall.*—Elongated, elliptical cluster.
- *Individual bud.*—Elliptical or oval.

Size when no color showing:
- *Overall.*—2.5–3 cm across cluster.
- *Individual bud.*—1.0–1.2 cm long; 0.5–0.7 cm wide.

Number of buds per cluster: 5–8.
Color (Just prior to sepals parting at tips): 52B.

INFLORESCENCE

Blooming habit: Continuous flowering throughout growing season; free and early blooming.
Size of umbel: 8–11 cm in diameter, 6 cm in depth.

Borne: Umbel, flowers on pedicel, pedicel on peduncle, 7–9 cm above foliage.

Flowers:

*Form.*—Cupped.

*Number of flowers per umbel.*—5–8.

*Size.*—Diameter: 5–5.3 cm. Depth: 1.8–2.2 cm.

Petals:

*Color.*—Upper surface: From the edges of the petal, 55A dominates until near the base of the petal where it fades to 38A and then directly to white, 155D. In the upper two petals, there is a presence of a white-eye, 155D, and venation of 58A which fades to 58B as the venation approaches the top of the petal. In the lower petals, venation is present in a lighter tone of 58B. Lower surface: 55B begins on the outer edges and fades to 38B and then to white, 155D. There is some speckling of white, 155D, throughout the petal's lower surface. Shape: Inverted teardrop; pointed base, rounded apex. Size: 2.7–3.2 cm long; 1.7–2.2 cm wide. Margin: Entire. Number per flower: 9–12. Texture and appearance: Highly reflective, smooth, velvety.

Tonality from a distance: A deep salmon pink flower, which has a ruffled appearance atop deep green cascading foliage.

Petaloids:

*Quantity.*—2–5.

*Shape.*—Irregular; some twisted; tubular.

*Color.*—Same as petals.

Sepals:

*Quantity.*—5.

*Shape.*—Narrow, nearly parallel at base, narrows to point; pointed apex, entire margin.

*Size.*—1.4–1.5 cm long; 0.3–0.6 cm wide.

*Color.*—Upper and lower surface: 144B.

Pedicel:

*Length.*—1.8–3 cm.

*Color.*—144A.

Peduncle:

*Length.*—9–14 cm.

*Color.*—144A.

Lasting quality: Umbels last 7–14 days; individual flowers last 7 days.

Disease/pest resistance: No susceptibility to diseases or pests has been noted to date.

REPRODUCTIVE ORGANS

Stamens:

*Anthers.*—1.5–2 mm in length.

*Filaments.*—Length: 1–1.1 cm. Color: White with pale pink tips. Pollen: Orange.

Pistils:

*Number.*—One.

*Length.*—1–1.2 cm.

*Stigma.*—Number: One. Color: Deep red.

*Style.*—Length: 4–5 mm. Color: White.

*Ovaries.*—Superior, pubescent, 4–5 cm long, 2 mm wide, green.

Fruit: None observed.

I claim:

1. A new and distinct variety of geranium plant substantially as shown and described.

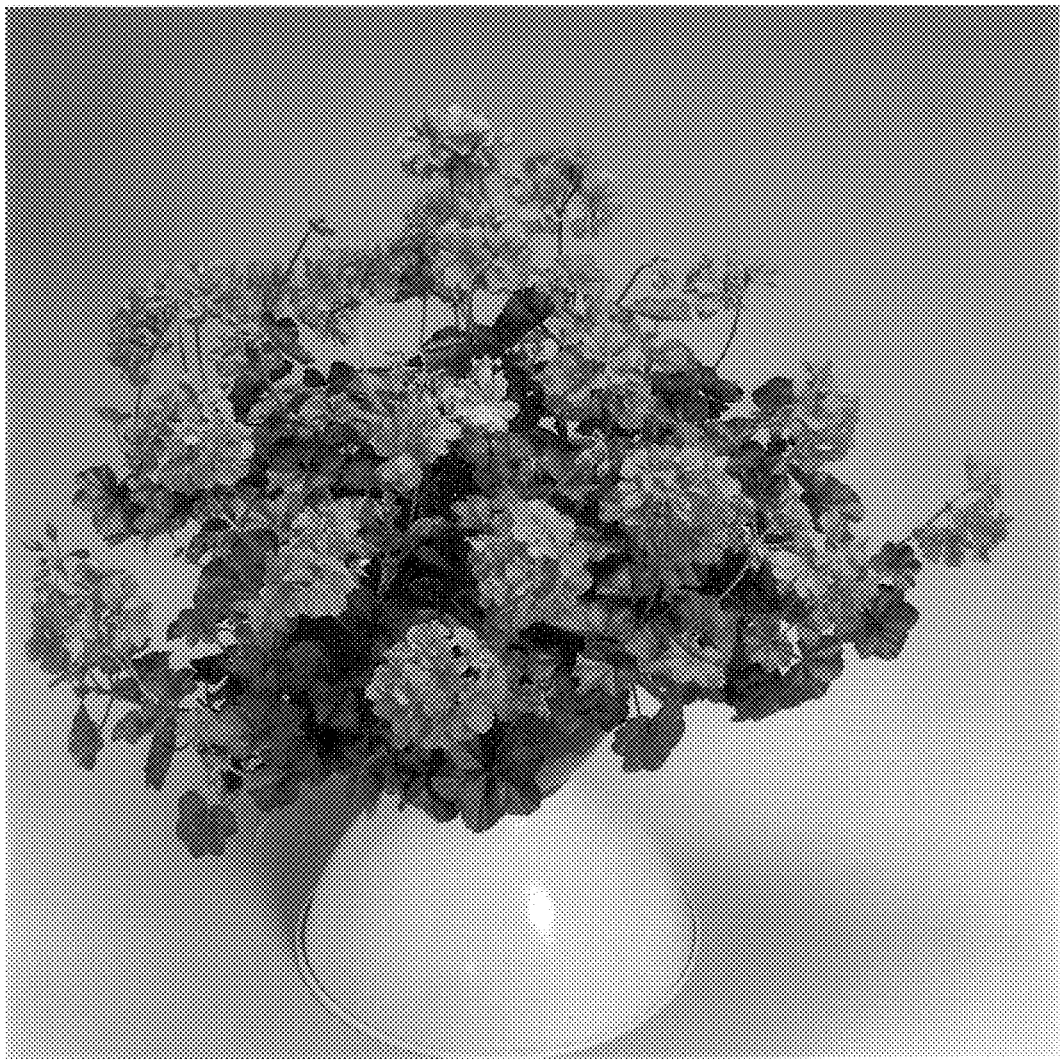

* * * * *